United States Patent
Sekine et al.

(10) Patent No.: US 7,273,451 B2
(45) Date of Patent: Sep. 25, 2007

(54) ENDOSCOPIC TREATMENT SYSTEM AND ANASTOMOTIC METHOD USING THIS SYSTEM

(75) Inventors: Ryuta Sekine, Koganei (JP); Keita Suzuki, Kokubunji (JP); Anthony Nicholas Kalloo, Glenn Dale, MD (US); Sergey Veniaminovich Kantsevoy, Silver Spring, MD (US)

(73) Assignee: Olympus Corporation, Tokyo (JP)

( * ) Notice: Subject to any disclaimer, the term of this patent is extended or adjusted under 35 U.S.C. 154(b) by 536 days.

(21) Appl. No.: 10/793,390

(22) Filed: Mar. 4, 2004

(65) Prior Publication Data
US 2004/0225191 A1    Nov. 11, 2004

Related U.S. Application Data

(60) Provisional application No. 60/451,714, filed on Mar. 4, 2003.

(51) Int. Cl.
*A61B 1/018* (2006.01)
*A61B 1/07* (2006.01)

(52) U.S. Cl. .................. 600/104; 600/156; 600/182; 600/117; 600/178

(58) Field of Classification Search ............ 600/101, 600/104, 156, 182, 117, 178; 128/898
See application file for complete search history.

(56) References Cited

U.S. PATENT DOCUMENTS

| | | | | |
|---|---|---|---|---|
| 3,131,690 A | * | 5/1964 | Innis et al. | 600/249 |
| 4,898,175 A | * | 2/1990 | Noguchi | 600/476 |
| 5,312,398 A | * | 5/1994 | Hobart et al. | 606/14 |
| 5,318,008 A | * | 6/1994 | Bullard | 600/139 |
| 5,423,321 A | * | 6/1995 | Fontenot | 600/476 |
| 5,441,507 A | * | 8/1995 | Wilk | 606/139 |
| 5,904,147 A | * | 5/1999 | Conlan et al. | 128/899 |
| 6,129,662 A | * | 10/2000 | Li et al. | 600/182 |
| 6,296,608 B1 | * | 10/2001 | Daniels et al. | 600/104 |
| 6,597,941 B2 | * | 7/2003 | Fontenot et al. | 600/473 |
| 6,685,666 B1 | * | 2/2004 | Fontenot | 604/27 |
| 2003/0135091 A1 | * | 7/2003 | Nakazawa et al. | 600/113 |

FOREIGN PATENT DOCUMENTS

JP    3211141    7/2001

* cited by examiner

*Primary Examiner*—John P. Leubecker
(74) *Attorney, Agent, or Firm*—Scully, Scott, Murphy & Presser, P.C.

(57) ABSTRACT

The endoscopic system includes an endoscope having an insertion portion which is inserted into a body and has a forceps insertion duct, and a light emitting member which has an end portion that emits the light and is inserted into a hollow organ in the body through the forceps insertion duct of the endoscope. The light emitting member issues positional information of the hollow organ which is detected through the endoscope orally and gastrically inserted into an abdominal cavity by causing the end portion to emit the light in the hollow organ. The system includes a treatment instrument by which a treatment is conducted in the abdominal cavity in cooperation with the endoscope.

23 Claims, 11 Drawing Sheets

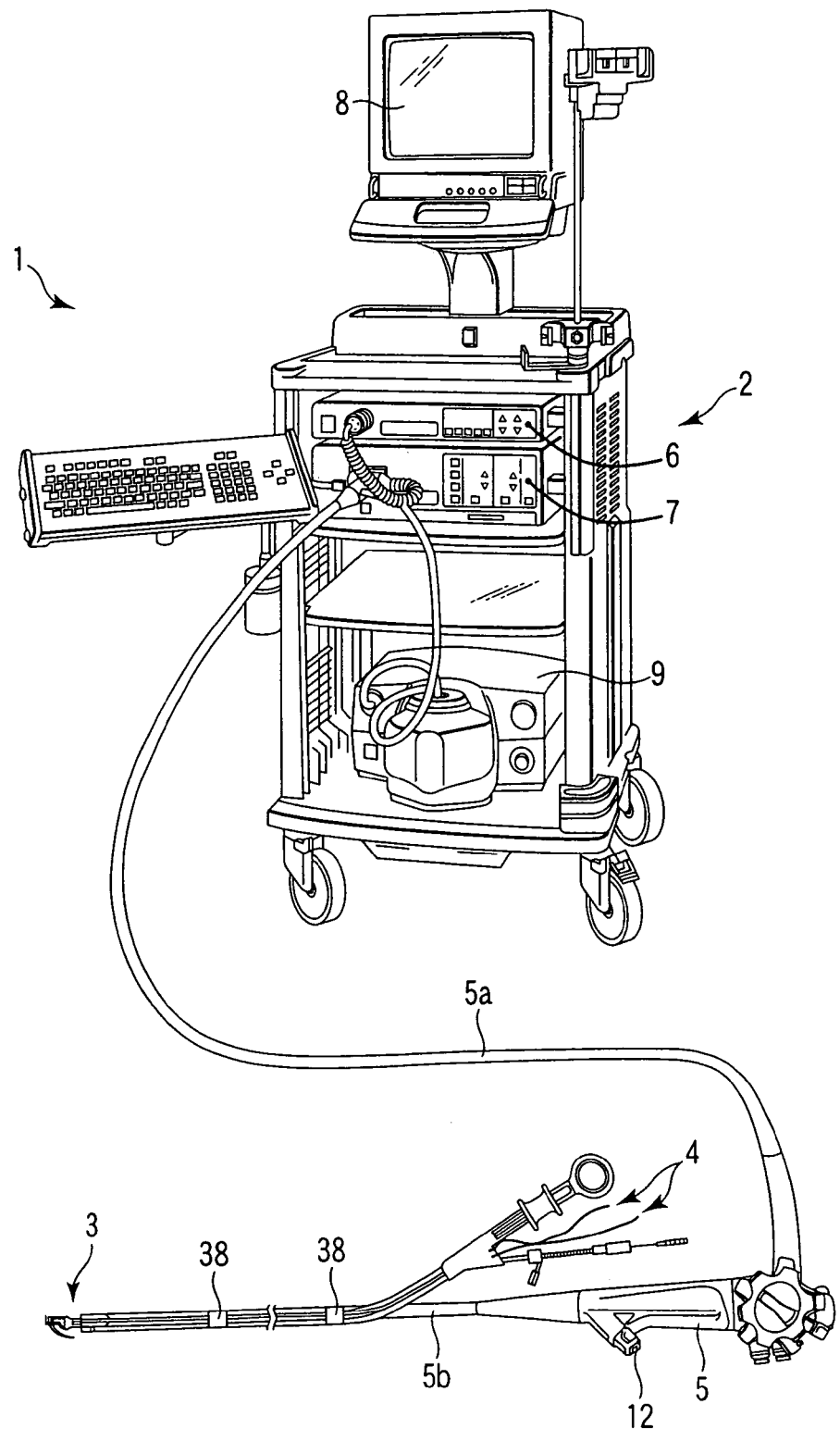
F I G. 1

ENDOSCOPIC TREATMENT SYSTEM AND ANASTOMOTIC METHOD USING THIS SYSTEM

CROSS-REFERENCE TO RELATED APPLICATIONS

This application claims the benefit of U.S. Provisional Application No. 60/451,714, filed Mar. 4, 2003.

BACKGROUND OF THE INVENTION

1. Field of the Invention

The present invention relates to an endoscopic intra-abdominal treatment system and an endoscopic gastrojejunostomy.

2. Description of the Related Art

Japanese Patent No. 32211141 discloses a coelomic duct identification apparatus which is inserted into a coelomic duct such as a bile duct, a pancreatic duct or a urethra which is thin and hard to be identified in an abdominal operation, and facilitates identification of this coelomic duct from the outside.

This coelomic duct identification apparatus includes a flexible tube having an end closed, and a light guide tube consisting of a light guide inserted into the flexible tube. This light guide has an optical fiber bundle in which positions of respective outgoing radiation ends are dispersed and arranged. The outgoing radiation ends emit the light for a predetermined length in an axial direction of the light guide tube. The entire bile duct can be irradiated with the light by inserting the light guide tube having this predetermined length formed longer than, e.g., the length of the bile duct and keeping it therein.

BRIEF SUMMARY OF THE INVENTION

According to one aspect of the present invention, there is provided an endoscopic treatment system comprising: an endoscope having an insertion portion orally inserted into a body and having a forceps insertion duct extended; and a light emitting member having an end portion that emits the light, and being inserted into a hollow organ in the body through the forceps insertion duct of the endoscope. The light emitting member issues positional information of the hollow organ which is detected through the endoscope orally and gastrically inserted into an abdominal cavity, by causing the end portion to emit the light in the hollow organ. The treatment system also includes a treatment instrument by which a treatment is conducted in the abdominal cavity in cooperation with the endoscope inserted into the abdominal cavity.

According to another aspect of the present invention, there is provided an endoscopic gastrojejunostomy procedure that comprises: orally inserting an endoscope into the duodenum; inserting a guide wire into the intestine through a forceps insertion duct of the endoscope; inserting the guide wire into a guide tube and inserting the guide tube into of the small intestine along the guide wire; confirming that the end of the guide tube has reached a target position in the small intestine based on an inserted length of the guide tube and/or fluoroscopy; providing an extension member to the proximal end portion of the guide tube protruding from the forceps insertion duct to the outside of the body; removing the endoscope while keeping the guide tube in the alimentary tract; removing the guide wire; removing the extension member from the guide tube and then inserting an illuminator into the guide tube; orally inserting an endoscope and an endoscopic guide tube into the stomach along the guide tube; incising the stomach wall by using the endoscope and the endoscopic guide tube and then advancing the endoscope into an abdominal cavity through this incision; confirming a target part in the small intestine by detecting the illuminator through the endoscope; and pulling the confirmed target part in the small intestine into the stomach and then conducting the gastrojejunostomy.

According to still another aspect of the present invention, there is provided an endoscopic gastrojejunostomy procedure that comprises: orally inserting an endoscope into the intestine duodenum; inserting a guide wire into the intestine through a forceps insertion duct of the endoscope; inserting the guide wire into a guide tube and inserting an illuminator into the small intestine along the guide wire; confirming that the end of the illuminator has reached a target part in the small intestine based on an inserted length of the illuminator and/or fluoroscopy; removing the endoscope and the guide wire while keeping the illuminator in the alimentary tract; orally inserting an endoscope and an endoscopic guide tube into the stomach along the guide tube; incising the stomach wall by using the endoscope and the endoscopic guide tube and then advancing the treatment endoscope into an abdominal cavity through this incision; confirming the target part in the small intestine by detecting the illuminator through the endoscope; and pulling the confirmed target part in the small intestine into the stomach and then conducting the gastrojejunostomy.

According to still another aspect of the present invention, there is provided an endoscopic treatment system that comprises: an elongated marker member which is inserted into a hollow organ in the endoscopic manner and kept at a necessary position. The marker member has energy generating member for generating at least one energy of energies including electromagnetic waves, radiation, and ultrasonic waves at least at a part thereof. The system also includes a sensor that is inserted into a body cavity in the endoscopic manner in order to detect an energy from the marker member through the wall part of the hollow organ, and an endoscope which is inserted into an abdominal cavity, orally and through a gastric incision, for conducting an endoscopic treatment at a part positioned based on information detected by the sensor.

According to still another aspect of the present invention, there is provided an endoscopic intra-abdominal treatment system that comprises: an endoscope which is orally inserted into a body and has an insertion portion having a forceps insertion duct extended, and an elongated optical marker having a portion that emits the light at least at a part of the optical marker and inserted into a hollow organ in the body through the forceps insertion duct of the endoscope. The optical marker causes the portion to emit the light in the hollow organ in the body. The endoscope is inserted into an abdominal cavity orally and through a gastric incision, and detects positional information of the hollow organ through the emission of the light. The system further includes a treatment instrument which conducts a treatment in the abdominal cavity in cooperation with the endoscope.

According to still another aspect of the present invention, there is provided an endoscopic treatment system that comprises: an endoscope having an insertion portion orally inserted into a body and having a forceps insertion duct extended; a light emitting member inserted into a hollow organ in the body through the forceps insertion duct of the endoscope and comprising an illumination device, a sheath which has an end portion and a proximal end portion and in which the illumination device is disposed, an end cap fluid-tightly provided at the end portion of the transparent sheath, a connector having a connector main body to which a light source device is connected, the light emitting member emitting the light by which positional information of the hollow organ is detected through the endoscope orally and gastrically inserted into an abdominal cavity; and a treatment instrument for conducting a treatment is conducted in the abdominal cavity in cooperation with the endoscope.

According to still another aspect of the present invention, there is provided an endoscopic treatment system that comprises: an elongated marker member inserted into a hollow organ in the endoscopic manner and being kept at a target position, and including energy generating means that generates energy at least at a part of the marker member; detecting means inserted into a body cavity in the endoscopic manner, for detecting the energy from the marker member through the wall part of the hollow organ; and an endoscope inserted into an abdominal cavity, orally and through a gastric incision, for conducting an endoscopic treatment at the target position based on information detected by the sensor.

BRIEF DESCRIPTION OF THE SEVERAL VIEWS OF THE DRAWING

FIG. 1 is a schematic view showing an entire endoscopic treatment system according to a preferred embodiment of the present invention;

FIG. 13 is an explanatory view showing the state that the endoscope having an over tube attached thereto approaches the stomach wall;

FIG. 14 is a view showing the state that the stomach wall is sucked by the over tube;

FIG. 15 is a view showing the state that the stomach wall is incised by a needle-shaped scalpel;

FIG. 16 is a view showing the state that a balloon dilator is inserted into an incision on the stomach wall and inflated;

FIG. 17 is a view showing the state that the endoscope is inserted into an abdominal cavity;

FIG. 18 is a view showing the state that the small intestine is grasped by grasping forceps and moved on the stomach wall side;

FIG. 19 is a view showing the state that a needle is pushed through the small intestine and a lifting thread is inserted in order to sling up the small intestine;

FIG. 20 is a view showing the state that the stomach and the small intestine are sutured by a curved needle suture machine;

FIG. 21 is a view showing the state that the small intestine is dissected by a needle-shaped scalpel;

FIG. 22 is a view showing the state that suture is conducted by the curved needle suture machine so as to open the small intestine mucous membrane;

FIG. 23 is a view showing the inside of the stomach from which a suture system is removed;

FIG. 25A is a schematic cross-sectional view showing the state that a hollow member and a front side body are connected while FIG. 25B is a schematic cross-sectional view showing an extension member which can be inserted between the hollow member and the front side body;

DETAILED DESCRIPTION OF THE PREFERRED EMBODIMENTS OF THE PRESENT INVENTION

FIGS. 1 to 7 show an endoscopic treatment system according to a preferred embodiment of the present invention. It is to be noted that an endoscopic suture machine is used in the embodiment mentioned below but a treatment instrument such as grasping forceps, thread cutter forceps, scissor forceps, hot biopsy forceps or a swivel clip device may be used in place of this machine.

Figure 2:
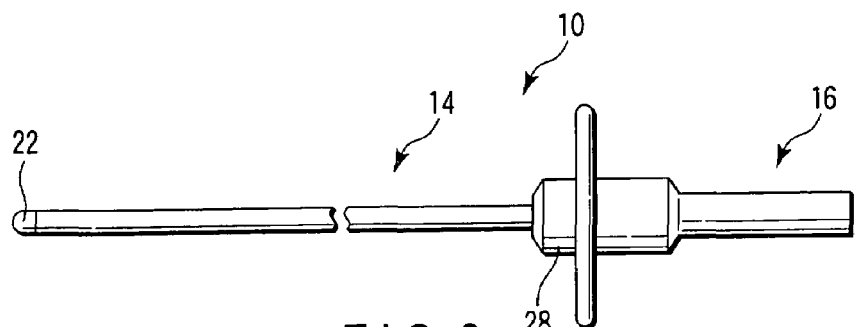
FIG. 2 is a schematic view showing an entire illuminator used together with the system depicted in FIG. 1.

As shown in FIG. 1, the endoscopic treatment system 1 according to this embodiment includes an endoscopic system 2, a suture machine 3, a suture thread 4 and an illuminator 10 (see FIG. 2).

The endoscopic system 2 includes an endoscope 5, an image processing device 6, a light source device 7, an observation monitor 8 and an aspirator 9, like a generally used electronic endoscopic system. The endoscope 5 is connected to the light source device 7 through a universal cord 5a, an image signal supplied from a CCD camera (not shown) provided at a distal end portion of an insertion portion 5b is processed in the image processing device 6 and then displayed on a monitor 13. The illustrated endoscope 5 having one forceps insertion duct 12 is used but one having two forceps insertion ducts may be used in place of this.

Further, like the general type, the endoscope 5 has a CCD camera, a light guide, a forceps insertion duct 12, and a nozzle for cleansing the lens of the CCD camera arranged at a distal end portion thereof. It is to be noted that a fiber endoscope having an eyepiece may be used in place of the electronic endoscope using the CCD. Although the suture machine 3 is detachably fixed to the insertion portion 5b of the endoscope 5 by a fixing member 38, the suture machine 3 may be constituted integrally with the endoscope 5 in place of this structure.

Figure 3:
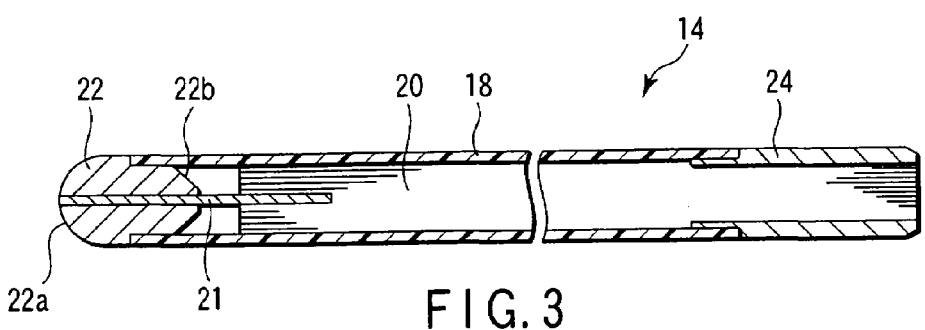
FIG. 3 is a schematic vertical cross-sectional view of a main body portion of the illuminator of FIG. 2.
Figure 4:
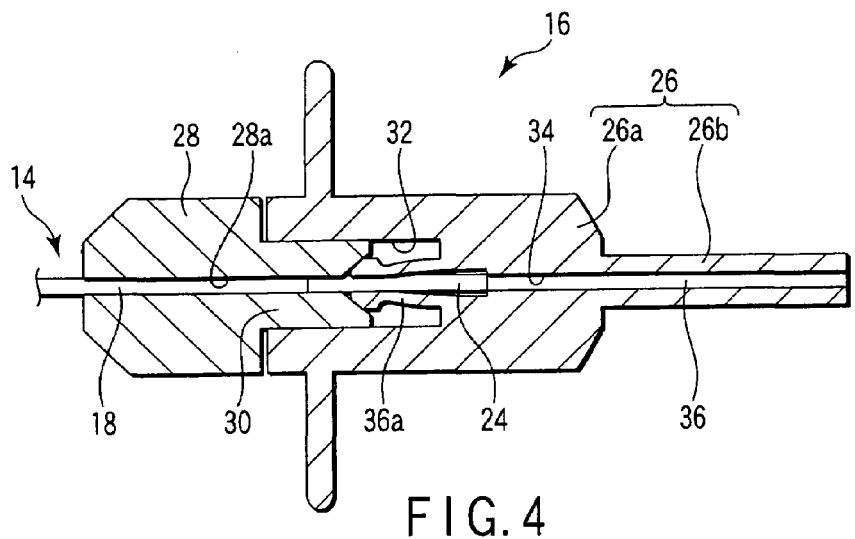
FIG. 4 is a schematic enlarged cross-sectional view of a joint portion of the main body portion and a connector portion of the illuminator depicted in FIG. 2.

As shown in FIGS. 2 to 4, the illuminator 10 includes an illuminator body 14 and a light guide connector (LG connector) 16 which optically connects the illuminator body 14 with the light source device 7. As shown in FIG. 3, the illuminator body 14 accommodates an optical fiber bundle 20 in a sheath 18 formed of a long hollow soft member made of transparent resin such as polyurethane, polyethylene, silicone, fluoroplastics, and a distal end portion of the transparent sheath 18 is closed to be fluid-tight, namely, so as to be capable of being sealed against both a liquid and a gas by an end cap 22 which is preferably formed of metal such as stainless steel, titanium or tungsten. This end cap 22 has a curved end surface 22a and a proximal end surface 22b having a substantially conical surface, and is fitted in the transparent sheath 18 to a substantially intermediate position. The spherical end surface 22a facilitates insertion of the illuminator 10, and the conical proximal end surface 22b of the end cap 22 acts as a reflecting surface which evenly reflects the light outgoing from the end surface of the optical fiber bundle 20 to the peripheral part through the transparent sheath 18.

Furthermore, a light guide connecting base (LG connecting base) 24 formed of a rigid material is fixed at the proximal end portion of the sheath 18. The proximal end portions of many optical fibers forming the optical fiber bundle 20 are integrally bonded in the LG connecting base 24 by an adhesive and firmly fixed to the LG connecting base 24. On the other hand, in the distal end portion of the optical fiber bundle 20, distal end portions of the respective optical fibers are uniformly cut, thereby forming a flat surface which is substantially orthogonal to the axis of the optical fiber bundle 20. Like the proximal end portions, the distal end portions of the many optical fibers are integrally bonded with adhesive. As a result, since the many optical fibers have the distal end portions and the proximal end portions being respectively integrated, the intermediate portion of the optical fiber bundle 20 can be bent in various directions. Moreover, the optical fiber bundle 20 does not move in the transparent sheath 18 even after repeating such bending, and the flatness of both end surfaces can be maintained.

It is to be noted that reference numeral 21 denotes a wire bonded to be fluid-tight and fixed to the distal end portion of the optical fiber bundle 20. This wire 21 is used when pulling the optical fiber bundle 20 into the transparent sheath 18, and the distal end portion of this wire is cut off so as not to protrude from the end cap 22.

As shown in FIG. 4, the LG connector 16 which optically connects the illuminator main body 14 with the light source device 7 has a connector main body 26 and a front side body 28 which detachably fixes a LG connecting base 24 to the connector main body 26. The LG connecting base 24 of the illuminator main body 14 is detachably fitted to the front side body 28 of the LG connector 16. This front side body 28 has a protrusion portion 30 having a male screw thereto protruding from the proximal end side, and the LG connecting base 24 protrudes from a central opening 28a opened on the proximal end side and surface of the protrusion portion 30. A circumferential portion of the central opening 28a is defined by a tapered surface converged on the distal end side.

On the other hand, the connector main body 26 to which the LG connecting base 24 is optically and mechanically connected has a main body portion 26a with which the front side body 28 is coupled and a rod portion 26b which protrudes from the proximal end side of this main body portion 26a and is optically connected to the light source device 7. To the main body portion 26a is formed a concave portion 32 having a female screw screwed into the protrusion portion 30 of the front side body 28. In addition, a central opening 34 is extended piercing the main body portion 26a and the rod portion 26b, and a rod lens 36 is accommodated on the proximal end side of the central opening 34, and bonded to the connector main body 26. The central opening 34 of the LG connector 16 is coaxially matched with the central opening 28a of the front side body 28 when the protrusion portion 30 of the front side body 28 is screwed into the concave portion 32.

Additionally, since the LG connecting base 24 is fixed being coaxially matched with the rod lens 36, the connector main body 26 has a plurality of fingers 36a, whose number is preferably three or more, extending to the distal end side from the circumferential portion of the opening end of the central opening 34 opened in the concave portion 32. It is preferable that these fingers 36a have a slight gap formed between the LG connecting base 24 and themselves and are arranged at equal distances in the radial direction and at equal intervals in the circumferential direction. The distal end of each finger 36a slightly expands to the outside. Therefore, when the protrusion portion 30 of the front side body 28 is fastened in the concave portion 32 of the LG connector 16, it is pressed toward the inside in the radial direction by the tapered surface defining the opening end of the central opening 28a, and the LG connecting base 24 can be fastened and fixed.

When connecting the illuminator main body 14 to the LG connector 16, the LG connecting base 24 of the illuminator main body 14 is inserted into the central opening 28a of the front side body 28, and the LG connecting base 24 is caused to protrude from the protrusion portion 30. Then, the distal end portion of the LG connecting base 24 is inserted into the central opening 34 of the connector main body 26 and comes into contact with the distal end surface of the rod lens 36. Thereafter, the protrusion portion 30 of the front side body 28 is screwed into the concave portion 32 of the connector main body 26. The front side body 28 presses the distal end portion of each finger 36 toward the inside in the radial direction while sliding against the LG connecting base 24. When a plurality of the fingers 36a are in contact with the LG connecting base 24 and the LG connecting base 24 is firmly fastened, the illuminator main body 14 and the LG connector 16 are optically and mechanically connected with each other. The light carried from the rod lens 36 passes through the optical fiber bundle 20 of the illuminator main body 14 and leaves the distal end surface, and is radiated in the circumferential direction from the reflecting surface 22b of the end cap 22.

It is noted that a diode (LED) may be used instead of an optical fiber bundle, and that at least a portion of the sheath at which light emitting member is disposed may be provided with transparent material.

Figure 5:
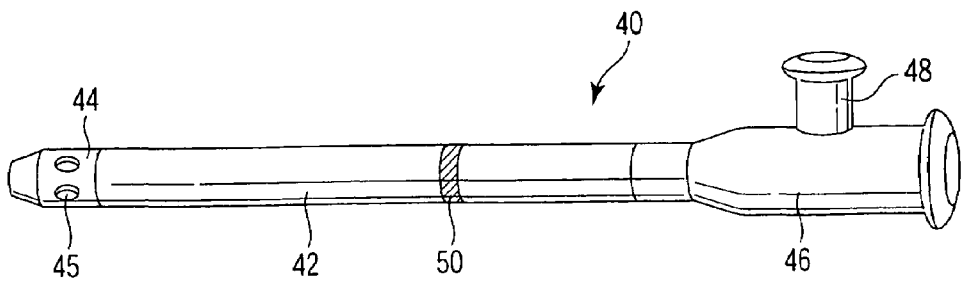
FIG. 5 is a schematic view showing an entire structure of a guide tube which guides the illuminator depicted in FIG. 2 into a body.

FIG. 5 shows a guide tube 40 for guiding an illuminator 10. The guide tube 40 may be inserted into, for example, the small intestine from the stomach through the forceps insertion duct 12 of the endoscope 5. The portion of the tube 40, which may be inserted into a patient, has a soft transparent hollow member 42. The hollow member 42 is made of resin or plastics such as polyurethane, polyethylene, silicone or fluoroplastics. A part of the hollow member 42 may be made of material that is opaque to X rays. The illuminator 10 may be inserted into the hollow member 42. An end chip 44 is fixed to the distal end of the hollow member 42. The chip 44 is made of material opaque to X rays, such as metal (stainless steel, titanium, tungsten, gold, platinum, or the like), resin or plastics. Further, a front side body 46 having an opening on the proximal end side is fixed to the proximal end portion of the hollow member 42, and an exhaust port 48 is provided at a side wall portion of the front side body 46. A valve or a cap which is usually closed but opened, e.g., when inserting the illuminator 10, can be arranged on the proximal end side opening of the front side body 46.

The distal end side of the end chip 44 is formed into a tapered shape, and the end chip 44 can be readily inserted into the forceps insertion duct 12 of the endoscope 5. Furthermore, the distal end of the end chip 44 forms thereto an opening into which the guide wire is inserted, and a plurality of side openings 45 are formed on the circumferential wall portion on the proximal end side. Forming such side openings 45 can facilitate sucking of intestinal fluids and air.

This guide tube 40 forms a marking 50 indicative of an insertion length at an appropriate part of the hollow member 42 forming the insertion portion. The number of the marking 50 is not restricted one as shown in the drawing, and a plurality of markings may be provided at adequate intervals according to needs. Arrangement of the insertion portion of the guide tube 40 and a position of the distal end portion in a hollow organ can be correctly informed based on a protrusion length of the endoscope 5 from the forceps insertion duct 12 by the marking 50 and detection of a position of the end chip 44 by fluoroscopy.

This guide tube 40 is formed in such a manner that a length of the hollow member 42 when the insertion portion, i.e., the end chip 44 is attached thereto is substantially twice or more that of the insertion portion 5b of the endoscope 5. Therefore, by arranging the distal end portion of the end chip 44 at a necessary position in, e.g., the small intestine and then removing the endoscope 5, the guide tube 40 can be kept in the body. Then, when the illuminator 10 is inserted from the opening on the proximal end side of the front side body 46, the illuminator 10 is guided along the guide tube 40. A position of the distal end portion of the illuminator 10 can be detected based on the insertion length in the guide tube 40. Generally, the distal end portion of the illuminator 10 is arranged in the vicinity of the end chip 44 of the guide tube 40. The light leaving the end surface of the optical fiber bundle 20 passes through the transparent hollow member 42 and reaches the outer side of the guide tube 40, and the inside of the hollow organ such as the small intestine is irradiate with this light. As a result, positional information concerning the hollow organ is output to the outside of the hollow organ.

Air, a gas, a liquid or the like accumulated inside the small intestine or the like during the therapy technique can be discharged to the outside of the body from the end opening of the end chip 44 and the side openings 45 through the exhaust port 48.

Figure 6A:
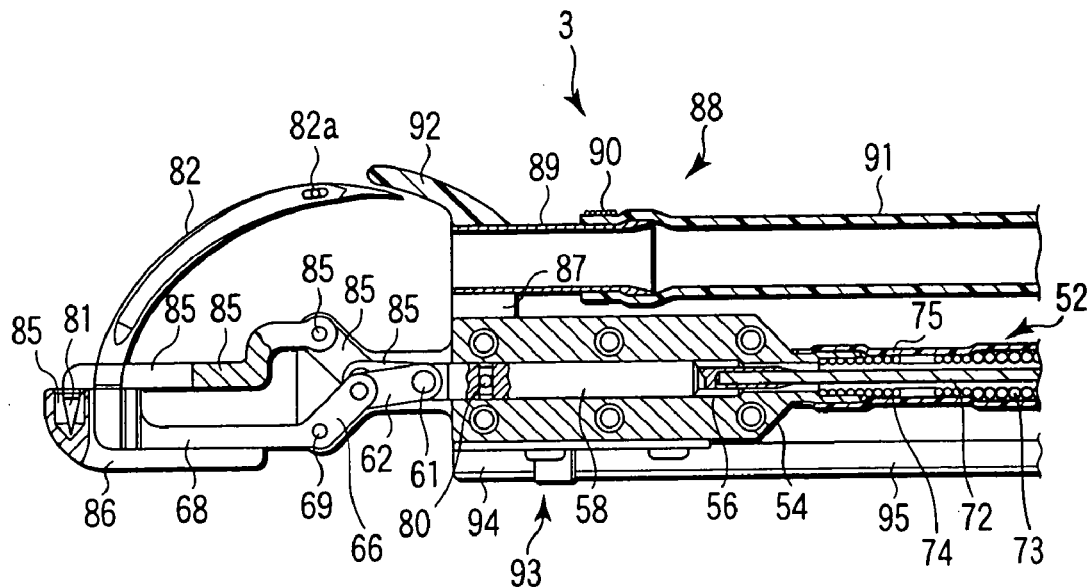
FIGS. 6A and 6B are a cross-sectional view and a side view respectively showing a closed state and an opened state of a suture machine used in the system depicted in FIG. 1.
Figure 6B:
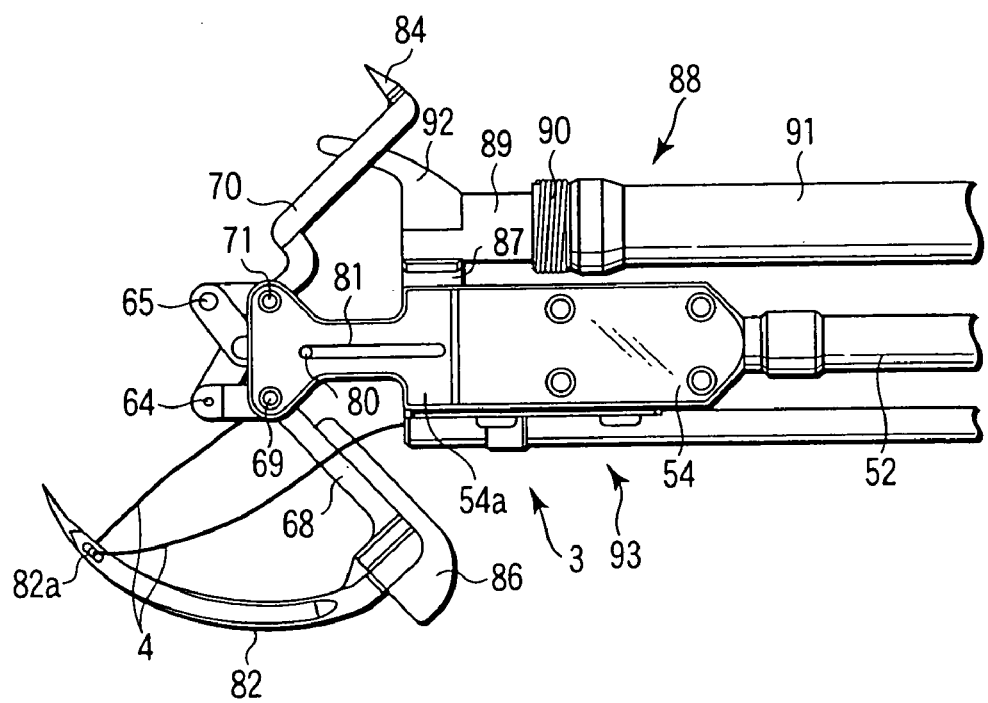

FIGS. 6A and 6B show the suture machine 3 which sutures a part of the small intestine confirmed based on the positional information provided by such an illuminator 10 on the stomach wall.

This suture machine 3 includes a flexible tube 52 and a holding member 54 which is fixed to the distal end portion and used to hold a later-described needle. To this holding member 54 are formed two support plate portions 54a opposed to each other with a gap therebetween and a hole 56 (see FIGS. 6A and 6B) communicating with the gap between these support plate portions and the inner hole of the flexible tube 73. A push rod 58 is arranged in the hole 56 so as to be capable of moving forward and backward along the axial direction.

One end of each of first and second connection members 62 and 63 is pivoted on the end of the push rod 58 through a pin 61. The other ends of the first and second connection members 62 and 63 are, respectively, pivoted on the proximal end portions of first and second arm members 66 and 67 through pins 64 and 65. Furthermore, a first activation member 68 integrally formed with the first arm member 66 is rotatably coupled with the support plate portion 54a through a pin 69. Likewise, a second activation member 70 integrally formed with the second arm member 67 is rotatably coupled with the support plate portion 54a through a pin 71.

The end of each of these pins 69 and 71 is formed by a small-diameter portion, and a dimension of the gap formed between the support plate portions 54a of the holding member 54 can be thereby maintained slightly larger than a sum of thicknesses of the first activation member 68 and the second activation member 70. The first activation member 68 and the second activation member 70 can move in the gap without producing large friction.

The push rod 58 is coupled with an elongated flexible transmission member 72. Moreover, the holding member 54 is coupled with coils 73 and 74 forming axial holes. The opposed end surfaces of these coils 73 and 74 are coupled with each other by laser welding, brazing, soldering or preferred means such as an adhesive. The coil 74 is formed of a strand having a smaller diameter than the coil 73, and the end side of the suture machine 3 is thereby formed to be readily bent. The entire lengths of these coils 73 and 74 are covered with a flexible tube 75 and held appressed against the flexible tube 75. The flexible tube 75 restricts expansion and contraction of the coils 73 and 74 in the axial direction, and the force to open/close the first activation member 68 and the second activation member 70 is thereby increased.

Figure 7:
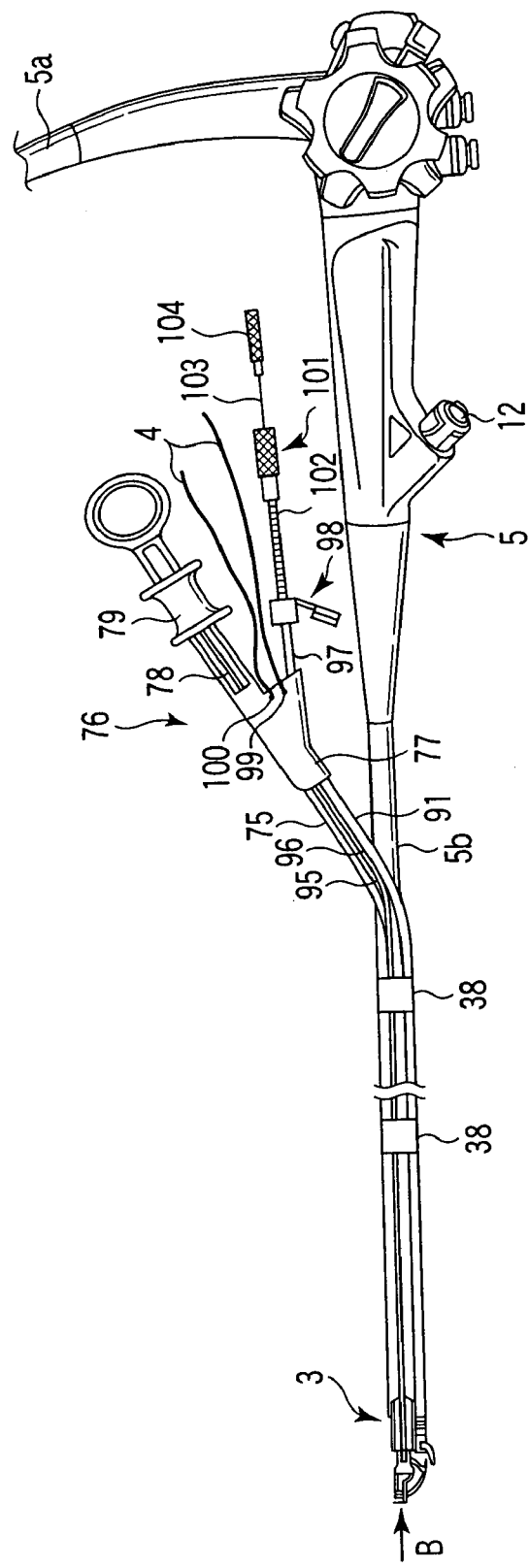
FIG. 7 is an enlarged view of the endoscope depicted in FIG. 1 and the suture machine.

As shown in FIG. 7, the proximal end portions of the flexible tube 75 and the coil 73 are fixed to an operation portion main body 77 of a suture machine operation portion 76. Moreover, the proximal end portion of the transmission member 72 is inserted into the operation portion main body 77 and coupled with a pipe 78 capable of sliding against the operation portion main body while being inserted into the pipe 76. This pipe 78 is connected to a movable member 79 by a non-illustrated coupling member. Therefore, when the movable member 79 is retired with respect to the operation portion main body 77, the first activation member 68 and the second activation member 70 can be opened/closed through the transmission member 72.

As shown in FIGS. 6A and 6B, the first and second arm members 66 and 67 can be passed between the pins 69 and 71 and opened to an angle shown in FIG. 6B. It is needless to say that appropriately setting the lengths of the first and second arm members 66 and 67 and the lengths of the first and second connection members 62 and 63 can increase or decrease an angle between the first and second arm members 66 and 67.

As shown in FIGS. 6A and 6B, a stopper pin 80 is fixed to the push rod 58. As shown in FIG. 6B, the stopper pin 80 is guided in a slit 81 which is formed to the holding member 54 and extends in the longitudinal direction, thereby restricting the motion of the first and second activation members 68 and 67 in the opening direction.

A curved needle 82 is fixed at the distal end of the first activation member 68. The curved needle 82 may be attached/detached with respect to the first activation member 68 in place of this structure. A needle hole 82a into which the suture thread 4 can be inserted is formed on the end side of the curved needle 82. In addition, a radial thickness of the curved needle 82 is reduced in order to improve pushing through living tissue.

The second activation member 70 has a bifurcated fixed arm 83, and two fixed needles 84 are respectively fixed at the end of the fixed arm 83. Although the fixed needles 84 are integrally fixed to the fixed arm 83 in this embodiment, they may be detachably disposed to the fixed arm 83. On the other hand, as shown in FIG. 6A, a protection member 86 having two holes 86 formed thereto is fixed to the first activation member 68 by a non-illustrated screw. As shown in FIG. 6A, this protection member 86 covers the needlepoint of the fixed needle 81 when the first and second activation members 68 and 70 are closed, and prevents the fixed needle 81 from being caught by, e.g., living tissue.

A channel member 88 is fixed at the holding member 54 through an L-shaped support member 87. This channel member 85 has a pipe 89 formed of a relatively hard material arranged at the end and a tube 91 formed of a relatively soft material which is press-fitted into this pipe and then fastened by a fixing thread 90, and this fixing thread 90 is fixed to the tube 91 by an adhesive. This pipe 89 is fixed to this support member 87 by brazing, soldering or appropriate means such as an adhesive.

Further, a protection member 92 is fixed to the pipe 89 by brazing, soldering or preferable means such as an adhesive. This protection member 92 covers a needlepoint of the curved needle 82 when the first and second activation member 68 and 70 are closed, in order to prevent the curved needle 82 from being caught by living tissue and the like.

Furthermore, two thread guides which guide the suture thread 4 between the suture machine operation portion 76 and the suture machine 3 are attached to the support member 87. The thread guide 93 shown in FIGS. 6A and 6B has a pipe 94 formed of a relatively hard material and a tube 95 formed of a relatively soft material, the pipe 94 is disposed to the support member 87, and the tube 95 is extended to the suture machine operation portion 76. Reference numeral 96 shown in FIG. 7 denotes a tube of the other thread guide.

As shown in FIG. 7, the tube 91 communicates with a mouth piece 97 coupled with the operation portion main body 77 on the front side thereof. A forceps tap 98 is provided to the front side of the mouth piece 97. Furthermore, the tubes 95 and 96 communicate with holes 99 and 100 formed to the operation portion main body 77 on their front sides, respectively.

Moreover, a thread grasping tool 101 used to grasp the suture thread 4 has a flexible tubular member 102 formed of a coil or the like and a pipe 103 which can move forward and backward in the tubular member 102. A hook provided at the distal end of the pipe 103 can be accommodated in or protrude from the flexible tubular member 102 by moving a grip 104 arranged on the proximal end side of the pipe 103 forward or backward. The suture thread 4 can slide on the hook when it is caught by the hook.

FIGS. 8 to 12 show the procedures of the gastrojejunostomy which bypasses the intestine duodenum D occluded by the cancer tissue T.

Figure 8:
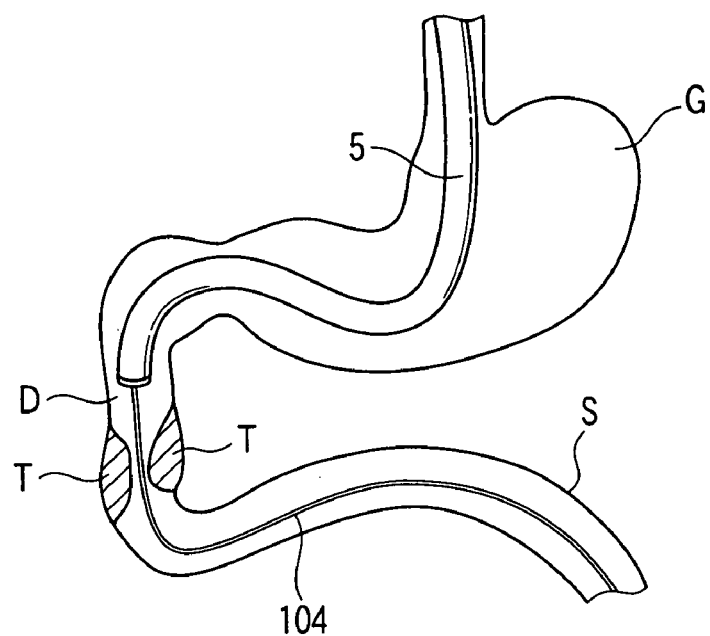
FIG. 8 is an explanatory view showing the state that a guide wire is inserted into the small intestine through the endoscope inserted into the stomach.

As shown in FIG. 8, the endoscope 5 (FIG. 7) is orally inserted into a deep part of the duodenum D from the stomach G. At that time, it is preferable to release the fixing member 38, remove the suture machine 3 from the insertion portion 5b and solely insert the endoscope 5. Of course, it is possible to prepare another endoscope to which no suture machine 3 is attached in advance and use this endoscope.

Figure 9:
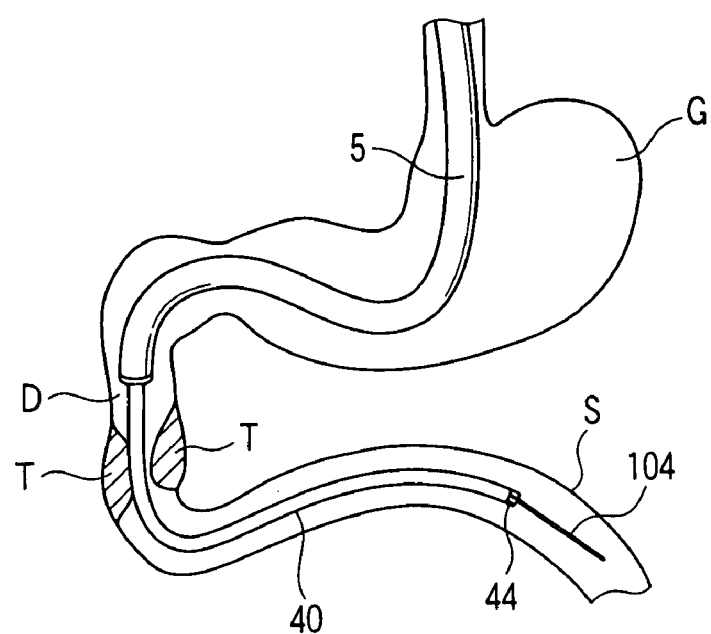
FIG. 9 is an explanatory view showing the state that the guide tube is inserted into a necessary part in the small intestine along the guide wire.

Subsequently, a guide wire 104 is inserted from the forceps insertion duct 12 of the endoscope 5, and the guide wire 104 is fed to a deep part of the small intestine S from the intestine duodenum D occluded by the cancer tissue T. Then, as shown in FIG. 9, the guide wire 104 is inserted into the guide tube 40 depicted in FIG. 5, and this guide tube 40 is likewise inserted to reach a deep part of the small intestine S from the forceps insertion duct 12 along the guide wire 104. At that time, using the marking 50 formed at the insertion portion of the guide tube 40 can confirm a length of insertion into the endoscope 5 or a protrusion length from the distal end of the endoscope 5. Moreover, detecting a position of the end chip 44 of the guide tube 40 by fluoroscopy can confirm a position of the end portion of the guide tube 40 in the small intestine S. In addition, after confirming that the end portion of the guide tube 40 has reached a target part in the small intestine, the endoscope 5 and the guide wire 104 are removed while the guide tube 40 is kept in the alimentary tract. At this moment, since the guide tube 40 is formed to be substantially double or more of the insertion portion 5b of the endoscope 5, the endoscope 5 can be completely removed from a patient.

Figure 10:
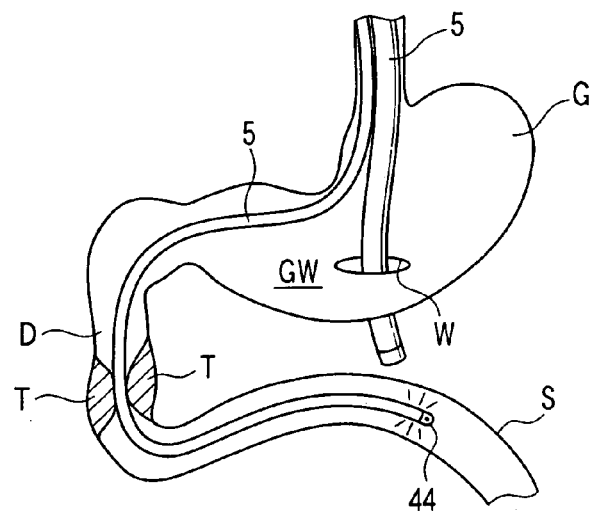
FIG. 10 is an explanatory view showing the state that the illuminator inserted into the guide tube is caused to emit the light and the illuminator is detected through the endoscope inserted into an abdominal cavity from the stomach wall.

Thereafter, as shown in FIG. 10, the endoscope 5 having the suture machine 3 attached thereto is orally inserted into the stomach G along the guide tube 40. Then, an incision h is formed by incising the stomach wall GW, and the distal end portion of the endoscope 5 is advanced into the abdominal cavity from the incision h. Concurrently, the illuminator 10 shown in FIG. 2 is inserted into the guide tube 40, and its end portion is arranged in the vicinity of the end chip 44 of the guide tube 40. The light led from the light source device 7 is caused to outgo from the end surface through the optical fiber bundle 20 of the illuminator main body 14. This light is reflected from the reflecting surface 22a of the end cap 22 in the circumferential direction and the wall part of the small intestine S is irradiated with this light. As a result, the necessary part in the small intestine can be detected through the endoscope 5 with the brightly illuminated part as a marker. At this moment, if the small intestine is inflated with air or intestinal fluids, the small intestine can be deflated by sucking air or the intestinal fluids to the outside through the guide tube 40, thereby facilitating detection by the endoscope 5.

Figure 11:
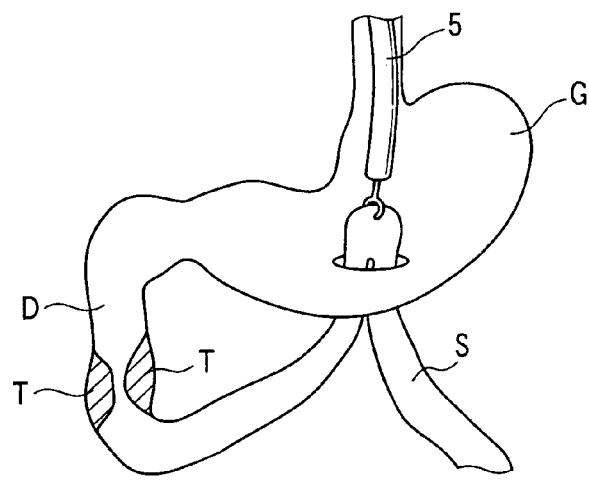
FIG. 11 is an explanatory view showing the state that the necessary part of the small intestine detected through a light emission portion is pulled into the stomach.
Figure 12:
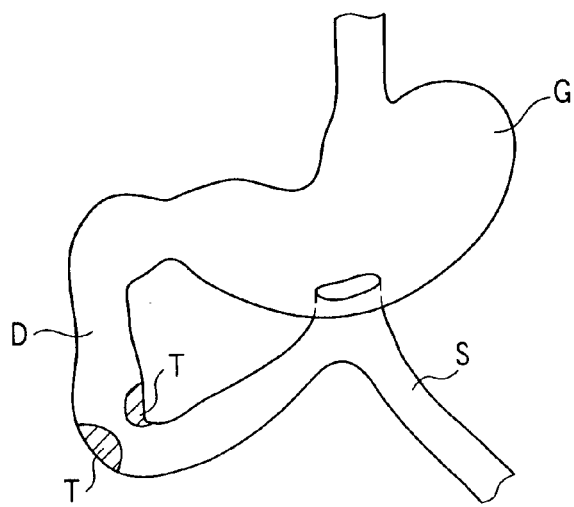
FIG. 12 is an explanatory view showing the state that the small intestine pulled into the stomach is anastomosed on the stomach wall.

As shown in FIG. 11, the part confirmed through the endoscope 5 is pulled into the stomach G by the forceps and, as depicted in FIG. 12, the small intestine S and the stomach wall GW are anastomosed. As a result, food in the stomach G of a patient can be directly supplied into the small intestine S. Such a stomach-small intestine anastomosis can be applied to an obesity treatment as well as a bypass treatment of the intestine duodenum stenosed by the cancer tissue.

FIGS. 13 to 23 show an example of the anastomotic procedure.

(1) It is preferable to insert the endoscope 5 into the over tube 106 together with the suture machine 3 assembled into the state shown in FIG. 7. At this moment, the suture thread 4 is inserted into the needle hole 82a of the curved needle 82, each end portion is passed through the thread guide and pulled to the outside of the suture machine 3 from the holes 99 and 100 of the operation portion main body 77, and this state is held. In addition, the endoscope 5 is previously connected to the image processing device 6, the light source device 7 and the like (FIG. 1) through the universal cord 5a. Thereafter, the over tube 106 having the suture machine 3 and the endoscope 5 accommodated therein is inserted into the stomach G through the mouth of a human body while observing the body cavity by the monitor 8.

Figure 13:
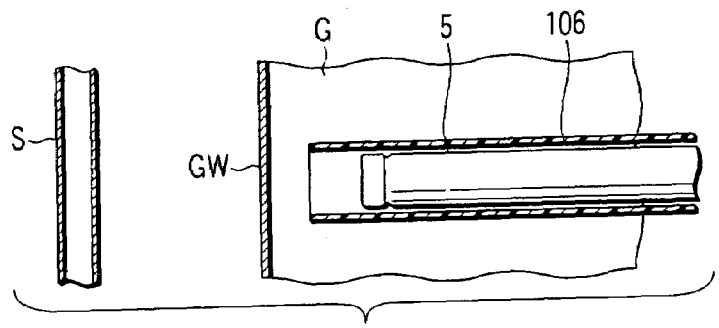
FIGS. 13 to 23 illustrate procedures to anastomose the small intestine on the stomach wall.

(2) As shown in FIG. 13, the over tube 106 is advanced toward the necessary part in the stomach G.

Figure 14:
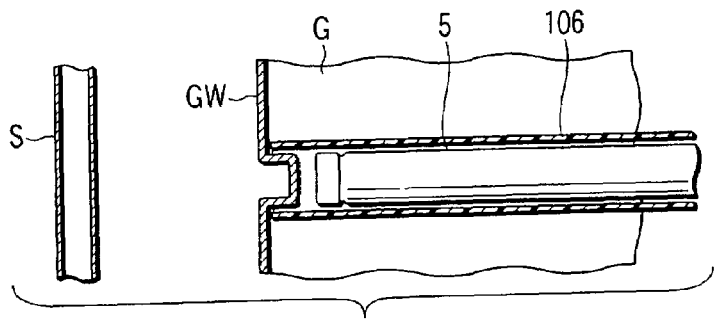

(3) As illustrated in FIG. 14, the over tube 106 is further moved forward and the distal end portion is brought into contact with the stomach wall GW. Then, the stomach wall GW is sucked by a non-illustrated aspirator through the over tube 106 or by a suction function of the endoscope 5. The stomach wall GW is sucked into the over tube 106, thereby forming a recession. When sucking the stomach wall, connecting a non-illustrated suction tube with the over tube 106 can form a path having a larger cross section than that of the channel of the endoscope 5 even if the endoscope 5 is inserted. Therefore, the suction action can be effected through the path or the inner hole in the over tube 106 having the smaller duct resistance, thereby forming a larger recession in a short period.

Figure 15:
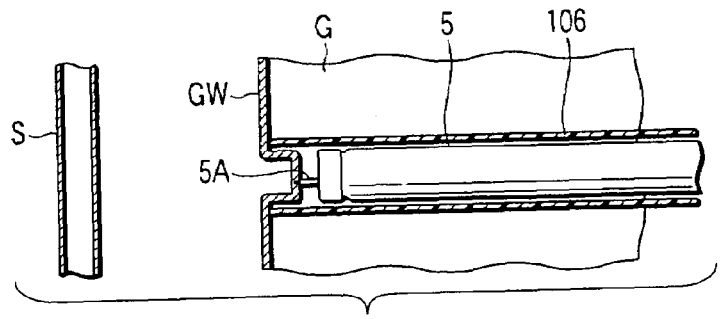

(4) As shown in FIG. 15, the needle-shaped scalpel 5A is inserted from the forceps opening channel 12 (see FIG. 7) of the endoscope 5 and caused to protrude from the distal end portion of the endoscope 5. The needle-shaped scalpel 5A is brought into contact with the stomach wall GW on which the recession is formed, a high-frequency current is supplied from a non-illustrated high-frequency power supply, and the stomach wall GW is perforated. Holding the recession on the stomach wall GW by the over tube 106 causes the stomach wall to be securely fixed by the over tube, and the stomach wall can be distanced from another organ close to the stomach G, e.g., the small intestine S. As a result, the necessary part on the stomach wall GW can be perforated without damaging any other organ close to the stomach wall GW. The needle-shaped scalpel 5A used to perforate the stomach wall GW may have an ordinary structure.

Figure 16:
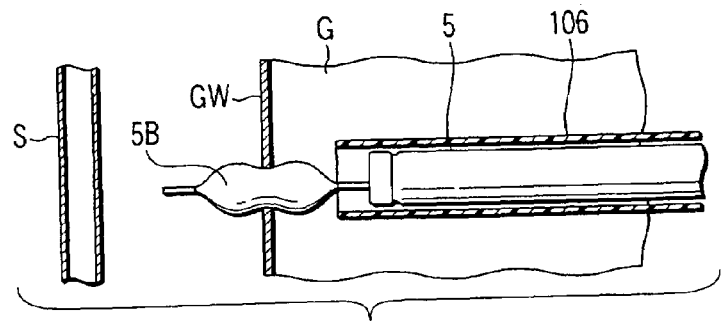

(5) After perforating the stomach wall GW, the balloon dilator 5B is inserted into the stomach G in place of the needle-shaped scalpel 5A. The balloon dilator 5B is inserted into the perforated part on the stomach wall GW, and this perforated part is expanded to a dimension enabling insertion of the end portion of the endoscope 5. FIG. 16 shows this state. The balloon dilator 5B used to expand the perforated part may have an ordinary structure, and it is preferable to have a peanut-like shape as shown in the drawing. After the balloon dilator 5B is inserted until the central portion thereof pierces the stomach wall GW, the balloon dilator 5B is inflated into the peanut-like shape shown in FIG. 16 by supplying a fluid by a non-illustrated inflation device. After the balloon dilator 5B is inflated to a size enabling insertion of the endoscope 5 into the perforated part on the stomach wall GW, supply of the fluid is stopped.

Figure 17:
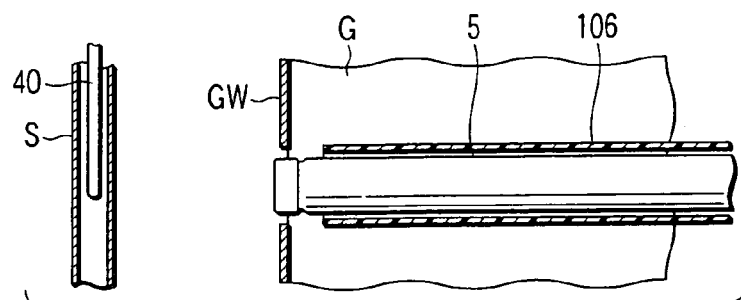

(6) As shown in FIG. 17, the end portion of the endoscope 5 is inserted into the expanded perforated part. The end portion of the endoscope 5 is further inserted toward the outer side of the stomach wall GW, i.e., into the abdominal cavity, and the end portion of the endoscope 5 is caused to be opposed to the part in the small intestine to be anastomosed. At this moment, illumination of the end portion of the illuminator 10 inserted into the guide tube 40 as described above can facilitate confirmation of the necessary part in the small intestine S.

Figure 18:
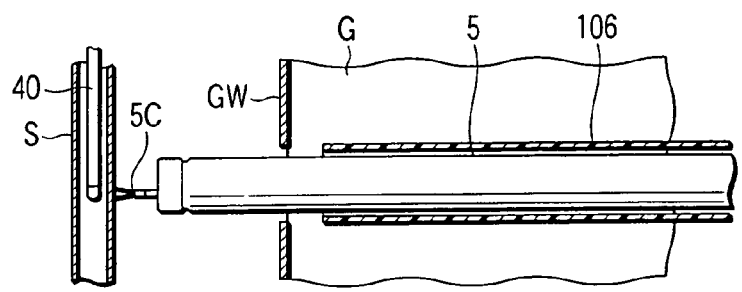

(7) Then, as shown in FIG. 18, the grasping forceps 5C is inserted into the abdominal cavity through, e.g., the forceps insertion duct 12 of the endoscope 5. The small intestine S is grasped by the grasping forceps 5C and brought to the stomach wall GW side. At that time, it is preferable to enter the state of FIG. 19 by pulling a part of the small intestine S into the stomach G from the perforated part on the stomach wall. At this moment, as shown in FIG. 11, removal of the illuminator 10 and the guide tube 40 is preferable.

Figure 19:
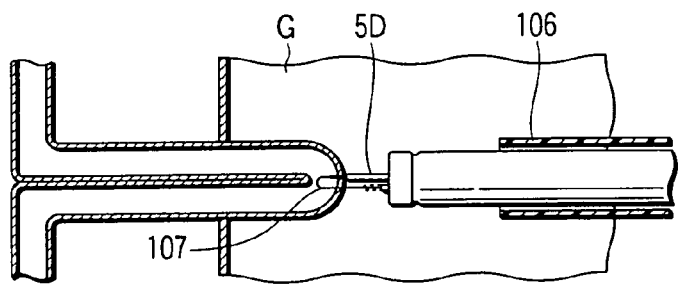

(8) As shown in FIG. 19, the needle 5D is put through the small intestine S pulled into the stomach G, and the thread 107 is inserted into this small intestine. This thread 107 is used to sling up the small intestine and prevents the small intestine from protruding toward the outside from the stomach wall GW. Both end portions of the thread 107 can be extended to the outside of the body and fixed at the part outside the body.

Figure 20:
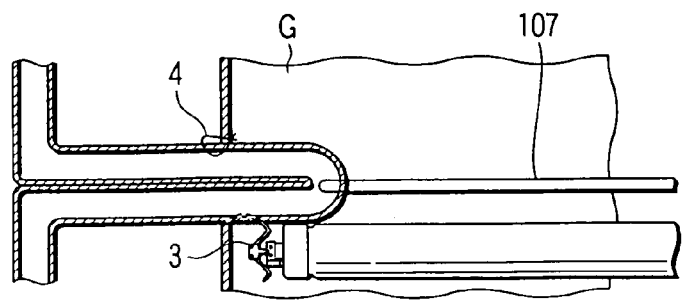

(9) As shown in FIG. 20, the circumferential part of the small intestine S lifted by the thread 107 is anastomosed to the inner peripheral part of the perforated part on the stomach wall GW. This suture can be conducted by using the above-described curved needle suture machine 3. It is to be noted that the procedures (1) to (8) can be performed by using the regular endoscope having no suture machine 3 fixed thereto without utilizing the endoscope 5 to which the suture machine 3 is fixed. In this case, suture can be conducted by inserting the endoscope 5 having the suture machine 3 fixed thereto from the mouth as shown in FIG. 7 only in the procedure requiring the suture machine 3.

Figure 21:
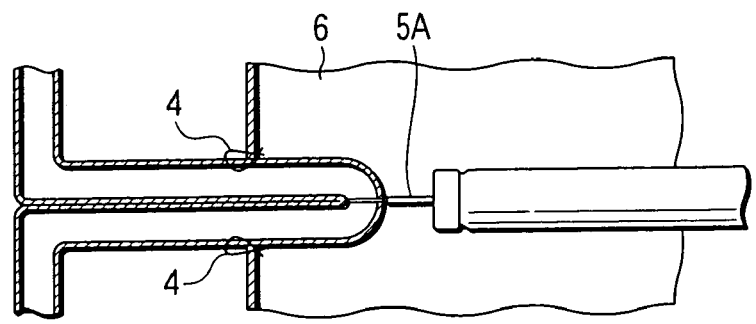

(10) Then, as shown in FIG. 21, the needle-shaped scalpel 5A is inserted into the stomach G, and the necessary part in the small intestine S pulled into the stomach G is dissected. It is to be noted that it is preferable to remove the thread for lifting 107 after dissecting the small intestine by the needle-shaped scalpel 5A but it may be removed before dissection. That is because the small intestine S is sutured along the inner peripheral part of the perforated part on the stomach wall GW.

Figure 22:
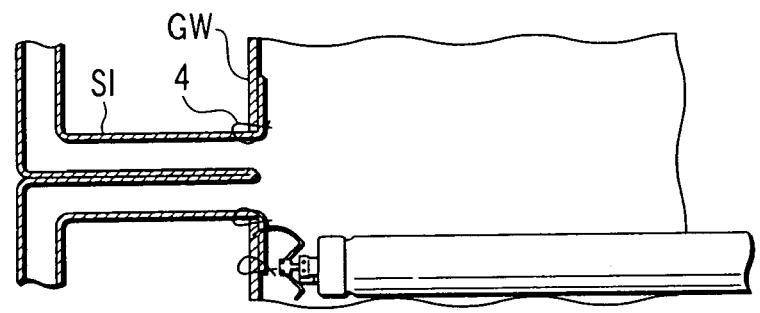

(11) Subsequently, as shown in FIG. 22, suture is made to the stomach wall GW by using the curved needle suture machine 3 so as to open the small intestine mucous membrane from the part dissected by the needle-shaped scalpel 5A.

Figure 23:
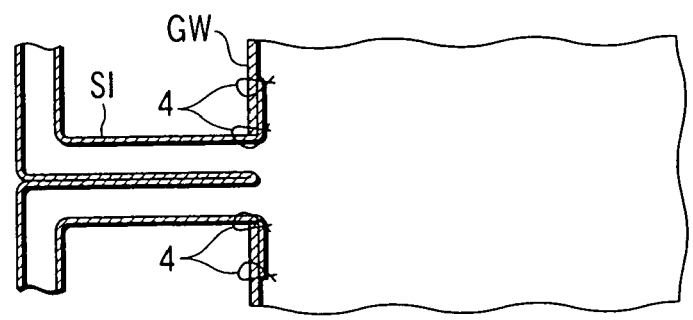

(12) The gastrojejunostomy is completed by removing the suture machine 3 which has finished suture from the stomach G together with the endoscope 5. FIG. 23 shows this state.

By conducting the gastrojejunostomy using the endoscope 5 orally inserted into the stomach G in this manner, the body surface of the living body does not have to be dissected, and the burden on a patient can be greatly reduced. Additionally, the illuminator 10 illuminates the part to be anastomosed in advance, and hence that part can be readily and securely confirmed by the endoscope inserted into the abdominal cavity through a gastric incision.

It is to be noted that such an anastomosis is not restricted to the above-described procedures, and it is possible to use various kinds of procedures, methods or instruments disclosed in the provisional application No. 60/365,687 (the non provisional application Ser. No. 10/390,443 filed on Mar. 17, 2003) entitled "ANASTOMOSIS SYSTEM" filed on Mar. 19, 2002, for example, therefore, the entire contents of which are incorporated herein by reference.

It is to be noted that such an anastomosis can be applied to anastomosing other hollow organs as well as anastomosing the stomach and the small intestine.

Figure 24:
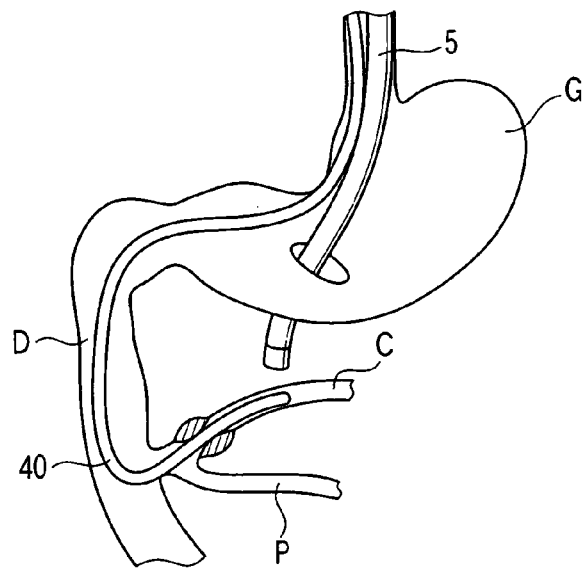
FIG. 24 is a view similar to FIG. 10, showing the state that the bile duct is anastomosed on the stomach wall.

FIG. 24 shows an example of bypassing a stenosed part in the bile duct C and anastomosing the stomach and the bile duct C. Reference character P designates the pancreatic duct. In this case, the above-described guide wire 104 (see FIG. 8) is inserted into the bile duct C in the endoscopic manner, and the guide tube 40 is inserted into the bile duct C along the guide wire. Then, after removal of the guide wire, the illuminator 10 is inserted into the guide tube 40 and kept at a necessary position. When pulling the bile duct C into the stomach G, the bile duct C must be carefully peeled from the liver. Further, the guide tube 40 and the illuminator 10 can be inserted into the pancreatic duct P when necessary. As a result, the bile duct C or the pancreatic duct P can be readily confirmed through the endoscope 5 orally or through a gastric incision inserted into the abdominal cavity, thereby facilitating the endoscopic intra-abdominal treatment.

Figure 25A:
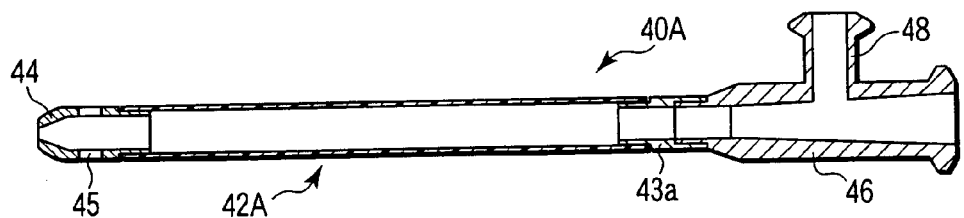
FIGS. 25A and 25B show a guide tube according to a modification.
Figure 25B:

FIGS. 25A and 25B show a guide tube 40A according to a modification.

As to this guide tube 40A, the elongated hollow member 42 is divided into a distal end side hollow member 42A and a proximal end side hollow member 42B, and the proximal end side hollow member 42B is formed as a detachable extension member. Therefore, a coupling tool 43a which can be coupled with the end of the front side body 46 is provided at both the proximal end portion of the distal end side hollow member 42A and the proximal end portion of the proximal end side hollow member 42B, and the coupling tool 43a and a detachable coupling tool 43b are provided to the distal end portions of the proximal end side hollow member 42B. If the guide tube 40A can maintain the outside diameter enabling insertion into the forceps insertion duct 12 of the endoscope 5 with the hollow members 42A and 42B being coupled therewith, it is possible to adopt an appropriate form such as a screw, snapping or pinning for the coupling tools 43a and 43b. Furthermore, the guide tube can be divided into three or more parts in case of need.

When using the guide tube 40A, the distal end side hollow member 42A and the proximal end hollow member 42B are coupled with the front side body 46 in advance before inserting the guide tube 40A into the forceps insertion duct 12. Then, before inserting the illuminator 10, namely, after removing the endoscope 5 and the guide wire 104 from the body, the proximal end hollow member 42B is removed. As a result, the length of the guide wire 104 to be kept in the body can be reduced, thereby facilitating the handling. Moreover, if needed, the guide wire 104 can be restored to the length which is substantially twice or more that of the insertion portion 5b of the endoscope 5 by coupling the proximal end hollow member 42B.

Figure 26:
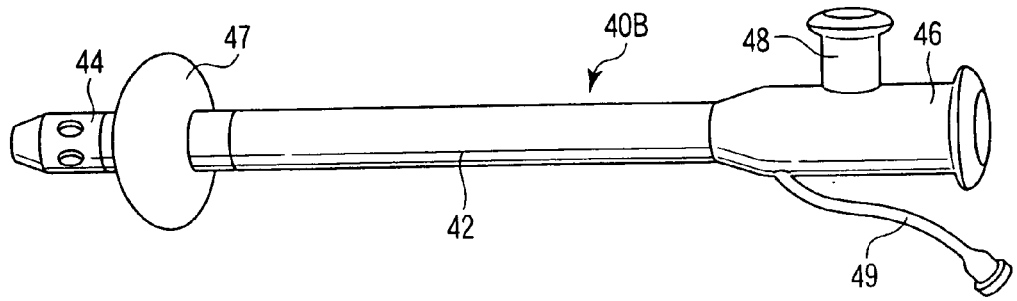
FIG. 26 is an explanatory view of a guide tube according to another modification.

FIG. 26 shows a guide tube 40B according to another modification.

This guide tube 40B has a transparent balloon 47 attached on the distal end side thereof. A fluid such as a gas or a liquid can be injected into or discharged from the balloon 47 through a balloon port 49 provided to the front side body 46. When keeping the distal end portion of the guide tube 40B in, e.g., the small intestine, inflation of the balloon 47 can avoid movement of this end portion. In addition, the inflated balloon 47 can avoid excessive air supply to the deep part in the small intestine and prevent accidental inflation of the small intestine during the therapy technique from being an obstacle of the therapy technique.

Figure 27:
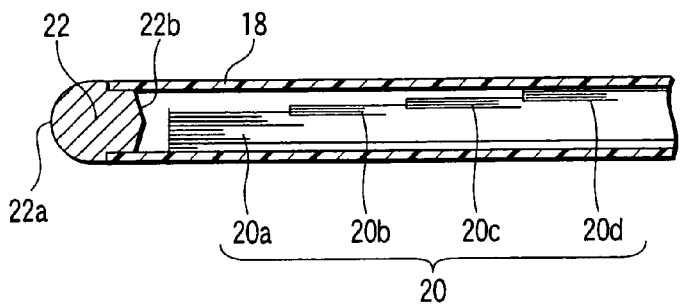
FIG. 27 is a schematic enlarged view of a main body portion of the illuminator according to a modification.
Figure 28:
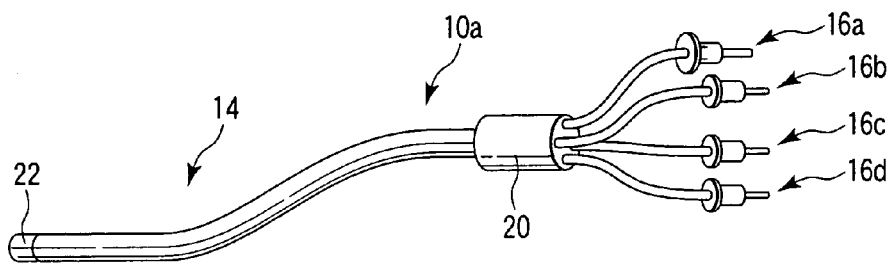
FIG. 28 is an explanatory view of the illuminator according to another modification.

FIGS. 27 and 28 show the illuminator 10A according to a modification.

In this illuminator 10A, the optical fiber bundle 20 is formed of a plurality of small optical fiber bundles 20a, 20b, 20c, 20c . . . having lengths different from each other. The distal end portions of these small optical fiber bundles are sequentially displaced and arranged, and form an illumination area extending along the axial direction. Additionally, the proximal end portions of the small optical fiber bundles extend to the proximal end portion side through the front side body 23 provided at the proximal end portion of the transparent sheath 18 and are connected to the LG connectors 16a, 16b, 16c, 16d, . . . optically connected to the light source device 7. Further, the light source device 7 can perform at least one of changing a quantity of light to be supplied to the respective small optical fiber bundles 20a, 20b, 20c, 20d . . . , sequentially guiding the light and changing the wavelength. In this case, it is preferable to obtain the maximum illumination by increasing the number of the optical fibers in the small optical fiber bundle 20a extending farthest to the distal end or supplying a maximum quantity of light.

It is to be noted that arranging on the same side all of the small optical fiber bundles 20b, 20c, 20d. . . except the small optical fiber bundle 20a extending farthest to the distal end as shown in the drawing is not required, and these small optical fiber bundles can be sequentially shifted and arranged in the circumferential direction and the axial direction with the small optical fiber bundle 20a in the center as long as illumination of each small optical fiber bundle can be confirmed.

By using such an illuminator 10A, a position of the distal end portion can be clearly displayed by using the brightest small optical fiber bundle 10a. Furthermore, a traveling direction of the hollow organ as well as a position of the same can be readily confirmed based on a change in a quantity of light, blinking, colors of the small optical fiber bundles 20b, 20c, 20d . . . shifted and arranged in the axial direction.

Figure 29:
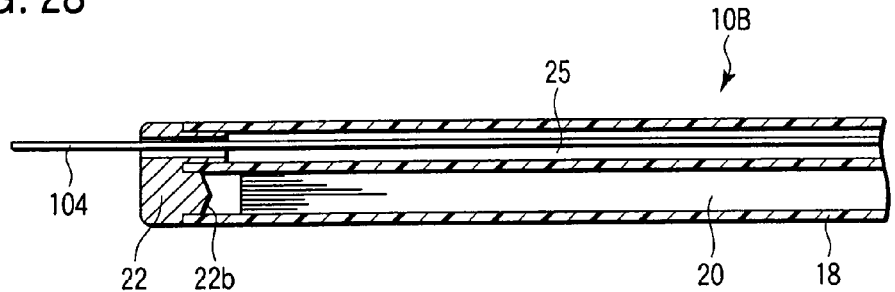
FIG. 29 is a schematic enlarged view showing a part of the main body portion of the illuminator according to still another modification.

FIG. 29 shows an illuminator 10B according to still another modification.

A channel 25 into which the guide wire 104 can be inserted is provided for this illuminator 10B. When inserting the illuminator 10B into the hollow organ, the previously inserted guide wire 104 can be inserted into the channel 25 to reach a necessary position. If the end cap 22 is formed of stainless steel which is the X-ray impermeable material as described above, a position in the body cavity can be detected by fluoroscopy. Moreover, when detecting an insertion length, a marking similar to that of the guide tube 40 can be made to an appropriate position on the outer peripheral surface of the transparent sheath 18.

As a result, only the illuminator 10B can be inserted into the hollow organ without using the guide tubes 40,40A and 40B mentioned above. The guide wire 104 can be removed after the end cap 22 is arranged at a necessary position. The channel 25 can be used to suck a liquid or a gas.

Figure 30:
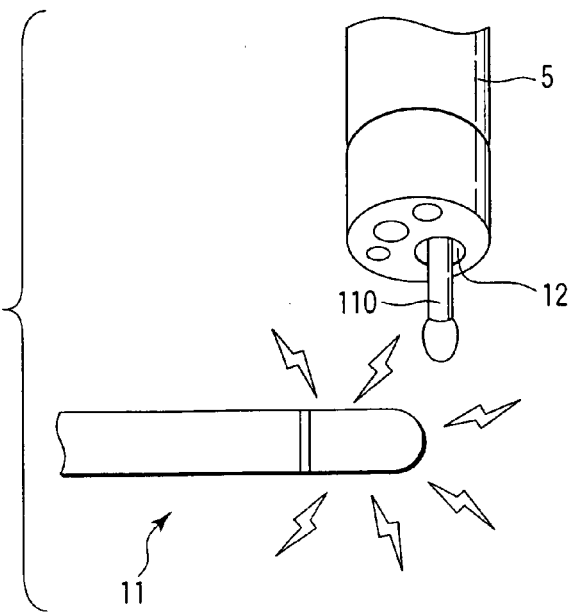
FIG. 30 is an explanatory view showing a marker member which generates an energy which can be detected in the endoscopic manner.

FIG. 30 shows a marker member 11 which generates at least one energy of energies including electromagnetic waves, radiation rays, ultrasonic waves and the like from the end portion in place of the light marker formed by the illuminators 10, 10A and 10B mentioned above. The energy emitted from the end portion of such a marker member 11 can be detected through a sensor 110 caused to protrude from the forceps insertion duct 12 opened at the end portion of the treatment endoscope 5.

It is to be noted that the respective members in the foregoing embodiments can be appropriately combined with each other and are not restricted to any single conformation.

What is claimed is:

1. An endoscopic treatment system comprising:
   an endoscope having an insertion portion configured to be inserted into a body and having a forceps insertion duct extended; and
   a light emitting member having an end portion that emits visible light, and being configured to be inserted into a hollow organ in the body through the forceps insertion duct of the endoscope,
   wherein the light emitting member issues positional information of the hollow organ which is visually detected through the endoscope inserted into an abdominal cavity, by causing a part of the end portion along an axial direction to emit the light in the hollow organ, and
   the system includes a treatment instrument configured to conduct a treatment in the abdominal cavity in cooperation with the endoscope inserted into the abdominal cavity.

2. A system according to claim 1, wherein the hollow organ into which the light emitting member is inserted is the small intestine.

3. A system according to claim 2, wherein the treatment is a gastrojejunostomy to anastomose the small intestine and the stomach wall.

4. A system according to claim 1, further comprising a light source device to which the light emitting member is connected,
   wherein the light emitting member comprises:
   an illuminator main body having an optical fiber bundle, a transparent sheath which has an end portion and a proximal end portion and into which the optical fiber bundle is inserted, an end cap fluid-tightly provided at the end portion of the transparent sheath, and a light guide connecting base provided at the proximal end portion of the transparent sheath; and
   a light guide connector having a connector main body which optically connects the iUuminator main body with the light source device, and a front side body which detachably fixes the light guide connecting base to the connector main body,
   and at least the end portion emits the light.

5. A system according to claim 4, wherein the light emitting member has a light emission area, along in the axial direction thereof, and at least in a part between the end portion and the proximal end portion, and the end portion is brighter than the light emission area.

6. A system according to claim 1, further comprising a light source device to which the light emitting member is connected,
   wherein the light emitting member includes:
   an illuminator main body having a plurality of optical fiber bundles having lengths different from each other, a transparent sheath which has an end portion and a proximal end portion and into which the optical fiber bundles are inserted, a fluid-tight end cap provided at the end portion of the transparent sheath, a light guide connecting base provided for each of the optical fiber bundles; and
   a light guide connector having a connector main body which optically connects each light guide connecting base with the light source device, and a front side body which detachably fixes the light guide connecting base to the connector main body,
   and the light source device performs at least one control including changing a quantity of light, sequentially guiding the light and changing a wavelength in accordance with each light guide connecting base.

7. A treatment system according to claim 1, further comprising a guide tube including a transparent soft hollow member which has an end portion and a proximal end portion and into which the light emitting member is inserted, an X-ray impermeable end chip provided at the end portion of the hollow member, a front side body provided at the proximal end portion of the hollow member, and an exhaust port provided to the front side body, and the guide tube is inserted into the forceps insertion duct of the endoscope.

8. A system according to claim 7, further comprising a guide wire which is inserted into the body through the guide tube,
   wherein the guide wire and the light emitting member is inserted into the guide tube, and the end portion of the guide tube has a hole having a dimension enabling insertion of the guide wire and disabling insertion of the end portion of the light emitting member.

9. A system according to claim 8, wherein the hollow member and the front side body of the guide tube are detachable and the guide tube has an extension member which is coupled between the hollow member and the front side body.

10. A system according to claim 9, wherein the guide tube has portions which are inserted into the forceps insertion duct of the endoscope when the extension member is coupled between the hollow member and the front side body, and the lengths of these portions are substantially twice or more the length of the insertion portion of the endoscope.

11. A system according to claim 7, wherein the light emitting member and the guide tube have portions which are inserted into the forceps insertion duct of the endoscope, and the lengths of these portions are substantially twice or more the length of the insertion portion of the endoscope.

12. The system according to claim 9, wherein the guide tube has an outer surface on which a marking showing an insertion length in the forceps insertion duct is formed.

13. An endoscopic gastrojejunostomy procedure comprising:
    orally inserting an endoscope into the duodenum;
    inserting a guide wire into the intestine through a forceps insertion duct of the endoscope;
    inserting the guide wire into a guide tube and inserting the guide tube into the small intestine along the guide wire;
    confirming that the end of the guide tube has reached a target position in the small intestine based on an inserted length of the guide tube and/or fluoroscopy;
    providing an extension member to the proximal end portion of the guide tube protruding from the forceps insertion duct to the outside of the body;
    removing the endoscope while keeping the guide tube in the alimentary tract;
    removing the guide wire;
    removing the extension member from the guide tube and then inserting an illuminator into the guide tube;
    orally inserting an endoscope and an endoscopic guide tube into the stomach along the guide tube;
    incising the stomach wall by using the endoscope and the endoscopic guide tube and then advancing the endoscope into an abdominal cavity through this incision;
    confirming a target part in the small intestine by detecting the illuminator through the endoscope; and pulling the confirmed target part in the small intestine into the stomach and then conducting the gastrojejunostomy.

14. An endoscopic gastrojejunostomy procedure comprising:
orally inserting an endoscope into the intestine duodenum;
inserting a guide wire into the intestine through a forceps insertion duct of the endoscope;
inserting the guide wire into a guide tube and inserting an illuminator into the small intestine along the guide wire;
confirming that the end of the illuminator has reached a target part in the small intestine based on an inserted length of the illuminator and/or fluoroscopy;
removing the endoscope and the guide wire while keeping the illuminator in the alimentary tract;
orally inserting an endoscope and an endoscopic guide tube into the stomach along the guide tube;
incising the stomach wall by using the endoscope and the endoscopic guide tube and then advancing the treatment endos cope into an abdominal cavity through this incision;
confirming the target part in the small intestine by detecting the illuminator through the endoscope; and
pulling the confirmed target part in the small intestine into the stomach and then conducting the gastrojejunostomy.

15. An endoscopic treatment system comprising:
a first endoscope having an insertion portion configured to be inserted into a body and having a forceps insertion duct extended;
an elongated marker member which is configured to be inserted into a hollow organ via the forceps insertion duct of the first endoscope and kept at a necessary position,
wherein the marker member has an energy generating member for generating at least one energy of energies including electromagnetic waves, radiation, and ultrasonic waves at least at a part thereof, and
the system includes:
a sensor configured to be inserted into a body cavity in the endoscopic manner in order to detect an energy from the marker member through the wall part of the hollow organ; and
a second endoscope which is configured to be inserted into an abdominal cavity, for conducting an endoscopic treatment at a part positioned based on information detected by the sensors,
wherein the marker member has a length which is twice or more than that of the forceps insertion duct of the first endoscope.

16. An endoscopic intra-abdominal treatment system comprising:
an endoscope which is configured to be inserted into a body and has an insertion portion having a forceps insertion duct extended; and
an elongated optical marker having a portion that emits light at least at a part of the optical marker, and being configured to be inserted into a hollow organ in the body through the forceps insertion duct of the endoscope,
wherein the optical marker causes the portion to emit the light in the hollow organ in the body,
the endoscope is configured to be inserted into an abdominal cavity orally and through a gastric incision, and detects positional information of the hollow organ through the emission of the light, and
the system includes a treatment instrument which is configured to conduct a treatment in the abdominal cavity in cooperation with the endoscope,
wherein the optical marker has a length which is twice or more than that of the forceps insertion duct of the endoscope.

17. An endoscopic treatment system comprising:
an endoscope having an insertion portion configured to be inserted into a body and having a forceps insertion duct extended;
a light emitting member configured to be inserted into a hollow organ in the body through the forceps insertion duct of the endoscope and comprising an illumination device, a sheath which has an end portion and a proximal end portion and in which the illumination device is disposed, an end cap fluid-tightly provided at the end portion of the sheath, a connector having a connector main body to which a light source device is connected, the light emitting member emitting the light by which positional information of the hollow organ is detected through the endoscope configured to be orally and gastrically inserted into an abdominal cavity; and
a treatment instrument configured to conduct a treatment in the abdominal cavity in cooperation with the endoscope,
wherein the sheath has an outer surface on which a marking showing an insertion length in the forceps insertion duct is formed.

18. A system according to claim 16, wherein at least a portion of the sheath at which the illumination device is disposed is provided with transparent material.

19. A system according to claim 17, wherein the illumination device comprises plural devices, each disposed at different positions in the axial direction of the sheath.

20. An endoscopic treatment system comprising:
a first endoscope having an insertion portion configured to be inserted into a body and having a forceps insertion duct extended;
an elongated marker member configured to be inserted into a hollow organ via the forceps insertion duct of the first endoscope and being kept at a target position, and including energy generating means that generates energy at least at a part of the marker member,
wherein the energy generating means has a length which is twice or more than that of the forceps insertion duct of the first endoscope, and an outer surface on which a marking showing an insertion length in the forceps insertion duct is formed,
detecting means configured to be inserted into a body cavity in the endoscopic manner, for detecting the energy from the marker member through the wall part of the hollow organ; and
a second endoscope configured to be inserted into an abdominal cavity, orally and through a gastric incision, for conducting an endoscopic treatment at the target position based on information detected by the sensor.

21. An endoscopic anastomy procedure comprising:
inserting an endoscope into a first hollow organ;
inserting a guide tube into the first hollow organ through the endoscope;
confirming that the end of the guide tube has reached a target position in the first hollow organ based on an inserted length of the guide tube and/or fluoroscopy;

providing an extension member to the proximal end portion of the guide tube protruding from a forceps insertion duct of the endoscope to the outside of the body;

removing the endoscope while keeping the guide tube in the first hollow organ;

removing the extension member from the guide tube and then inserting an illuminator into the guide tube;

inserting an endoscope and an endoscopic guide tube into a second hollow organ along the guide tube;

incising the wall of the second hollow organ by using the endoscope and the endoscopic guide tube and then advancing the endoscope into a body cavity through this incision;

confirming a target part in the first hollow organ by detecting the illuminator through the endoscope; and pulling the confirmed target part in the first hollow organ into the second hollow organ and then conducting the anastomy.

22. A procedure of bypassing a stenosed part in a bile duct and anastomosing a stomach and the bile duct, comprising:

inserting a guide wire into the bile duct in the endoscopic manner;

inserting a guide tube along the guide wire;

removing the guide wire from the body, inserting an illuminator emitting visible light into the guide tube, and keeping the illuminator at a predetermined position in the guide tube;

inserting an endoscope orally and gastrically into the abdominal cavity;

visually detecting the position of the bile duct via the endoscope through emission of the illuminator: and pulling a predetermined portion of the bile duct into the stomach to anastomose the stomach and bile duct.

23. The procedure according to claim 22, wherein a second illuminator is configured to be inserted into the pancreas before the predetermined portion of the bile duct is pulled into the stomach.

* * * * *